United States Patent
Barfoot et al.

(10) Patent No.: US 10,254,159 B2
(45) Date of Patent: Apr. 9, 2019

(54) POWER LIMITING METHODS FOR USE WITH OPTICAL SYSTEMS IN HAZARDOUS AREA LOCATIONS

(71) Applicant: Halliburton Energy Services, Inc., Houston, TX (US)

(72) Inventors: David A. Barfoot, Houston, TX (US); Mikko Jaaskelainen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 114 days.

(21) Appl. No.: 14/911,610

(22) PCT Filed: Oct. 7, 2013

(86) PCT No.: PCT/US2013/063648
§ 371 (c)(1),
(2) Date: Feb. 11, 2016

(87) PCT Pub. No.: WO2015/053738
PCT Pub. Date: Apr. 16, 2015

(65) Prior Publication Data
US 2016/0187194 A1 Jun. 30, 2016

(51) Int. Cl.
*G01J 1/04* (2006.01)
*G01J 1/44* (2006.01)
*G01N 21/47* (2006.01)

(52) U.S. Cl.
CPC .............. *G01J 1/0425* (2013.01); *G01J 1/44* (2013.01); *G01N 21/47* (2013.01); *G01N 21/474* (2013.01); *G01J 2001/444* (2013.01); *G01N 2021/4709* (2013.01); *G01N 2021/4742* (2013.01); *G01N 2201/088* (2013.01)

(58) Field of Classification Search
CPC ...... G01J 1/0425; G01J 1/44; G01J 2001/444; G01N 2021/4709; G01N 2021/4742; G01N 21/47; G01N 21/474; G01N 2201/088
USPC .................................................. 250/227.11
See application file for complete search history.

(56) References Cited

U.S. PATENT DOCUMENTS

| | | | |
|---|---|---|---|
| 5,394,419 A * | 2/1995 | Neuhaus | H01S 5/06825 372/29.012 |
| 6,061,493 A * | 5/2000 | Gilliland | G02B 6/4204 385/140 |
| 6,218,658 B1 | 4/2001 | Taneda et al. | |
| 7,021,836 B2 * | 4/2006 | Anderson | G02B 6/3881 385/48 |
| 7,325,982 B2 | 2/2008 | Aronson | |
| 7,840,098 B2 * | 11/2010 | Rong | G02F 1/025 385/1 |
| 2014/0268110 A1 * | 9/2014 | Hartog | G01D 5/35364 356/73.1 |

FOREIGN PATENT DOCUMENTS

| | | |
|---|---|---|
| JP | 2002-221740 A | 8/2002 |
| WO | 2008-020170 A2 | 2/2008 |
| WO | 2012-085802 A1 | 6/2012 |

* cited by examiner

Primary Examiner — Seung C Sohn
(74) Attorney, Agent, or Firm — Gilliam IP PLLC

(57) ABSTRACT

A fiber optic sensor interrogation system with inbuilt passive power limiting capability that provides improved safety performance for use in explosive atmospheres.

27 Claims, 4 Drawing Sheets

POWER LIMITING METHODS FOR USE WITH OPTICAL SYSTEMS IN HAZARDOUS AREA LOCATIONS

BACKGROUND

Fiber optic systems are used in many applications. One of the types of applications can be described as fiber optic sensor interrogators. In a typical fiber optic sensor interrogator, light is emitted from an interrogation unit containing a laser and other optical devices. The laser may be a continuous wave (CW) laser, it may be a pulsed laser, which may include a separate amplifier and pulse generator. Or it may be a naturally pulsed laser (for example a Nd:YAG laser) without need of separate amplification or pulsing circuitry. In addition, in a typical sensing application the interrogation system may contain an optical receiver to receive back-scattered signals from the sensor in order to make a measurement. In many applications, light that is emitted from the interrogator will reflect off of a sensor and return to the interrogator, for example a Fabry-Perot cavity, or fiber Bragg grating. Another method of sensing is to use the intrinsic backscattering of the fiber through scattering processes including Rayleigh, Brillouin, and Raman scattering. The scattering processes will provide a return signal back to the interrogator that is received at the detector to make a measurement of parameters like strain, vibration, and temperature.

An important design consideration in many fiber optic sensor interrogators is in applications in which the light from the interrogation unit passes into regions that that may contain explosive atmospheres, such as the subsurface environments of oil and gas wells.

Achieving intrinsic safety with any complex electrical device is very difficult because it requires that the available electrical energy at the device be limited below the level required for ignition. This requires that only low voltages and currents are used and that no significant energy storage can occur within the device. With a fiber optic sensor, the interrogator may be placed many tens or hundreds of meters away from the hazardous region with only the fiber optic cable and passive optical sensor being within the explosive atmosphere. For years it was thought that the energy present in fiber optic sensing systems was not high enough to cause ignition and additionally, all energy was contained inside the glass fiber, therefore it was safe to use in explosive atmospheres. However, in recent years, tests have been performed that demonstrate that in explosive atmospheres ideal for ignition, it is possible for a relatively low-power optical signal, on the order of 10s or 100s of milliwatts average power, to cause ignition. In the case of a broken fiber, optical power can exit the fiber and be absorbed by a small dust particle. The dust particle may absorb most of the optical power and due to its low surface area, heat can accumulate in the particle rapidly until the particle reaches a high enough temperature to cause ignition.

The optical power required for ignition depends on many factors including: core size of the fiber and beam diameter, pulse duration if pulsed light, wavelength of the light, components of the flammable gas mixture, and the presence of target particles. A number of experiments have been performed to determine a safe power threshold, below which ignition cannot occur even with the most explosive gas mixtures. A power level of 35 mW has been accepted as a safe threshold level, below which ignition due to optical radiation cannot occur.

These ignition power levels are not a concern for most fiber optic sensing systems when they are operating with normal power levels required for sensing. However, the capability exists within many of some interrogator designs to generate much higher power if a fault were to occur in the system. For example, a distributed sensing method like Distributed Temperature Sensing (DTS), Distributed Acoustic Sensing (DAS), etc. may interrogate a fiber optic sensing cable using an optical time domain reflectometry method whereby a short pulse of light, on the order of tens of nanoseconds or less, is sent into the fiber repeatedly at up to tens of kilohertz repetition rate. Typically, an electrical control circuit is used to generate the timing pulse, which is sent to an optical component that controls the timing and duration of the optical pulse. If a malfunction were to occur in this pulse generating circuit due to an electronics fault, or a fault in software/firmware that may be controlling the electronics, it will be possible for the optical pulse length to exceed the desired duration. In extreme cases, the pulse duration may grow to 10s or 100s or 1000s of times the normal duration, which will have the effect of increasing the average optical power by a proportional amount and may exceed the safe optical power level for operating in explosive atmospheres. Another possible fault may occur in any optical amplification component, for example an erbium-doped fiber amplifier (EDFA). The EDFA is given a control signal to set the gain to a desired level that is normally below the maximum gain that the EDFA is capable of generating. A fault in the electronics, firmware, or software controlling the EDFA may allow the gain level to exceed the desired level, allowing optical power levels to be emitted that are much higher than desired and may exceed the safety threshold for explosive atmospheres.

Prior art methods of power regulation, for example in fiber optic telecom systems, have been to use a device to monitor the power of the transmitted light by using a circulator/coupler to redirect a small percentage of the light to an optical detector. When the power indicated by the optical detector increases beyond a threshold value, an optical switch or variable optical attenuator is adjusted to attenuate the outgoing light. An electronic control circuit is used to coordinate these components. A disadvantage of such approaches though is that they involve active devices that have their own failure modes. If any one of these three components were to fail to operate properly, the safety mechanism may fail to operate.

There is a need then to move beyond these active systems to find in fiber optic interrogator systems that are more fail safe.

DETAILED DESCRIPTION

In this description then we offer a new approach by proposing a much safer fiber sensor interrogator than the prior art approaches.

In the following detailed description, reference is made that illustrate embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken in a limited sense, and the scope of the disclosure is defined only by the appended claims.

Figure 1:
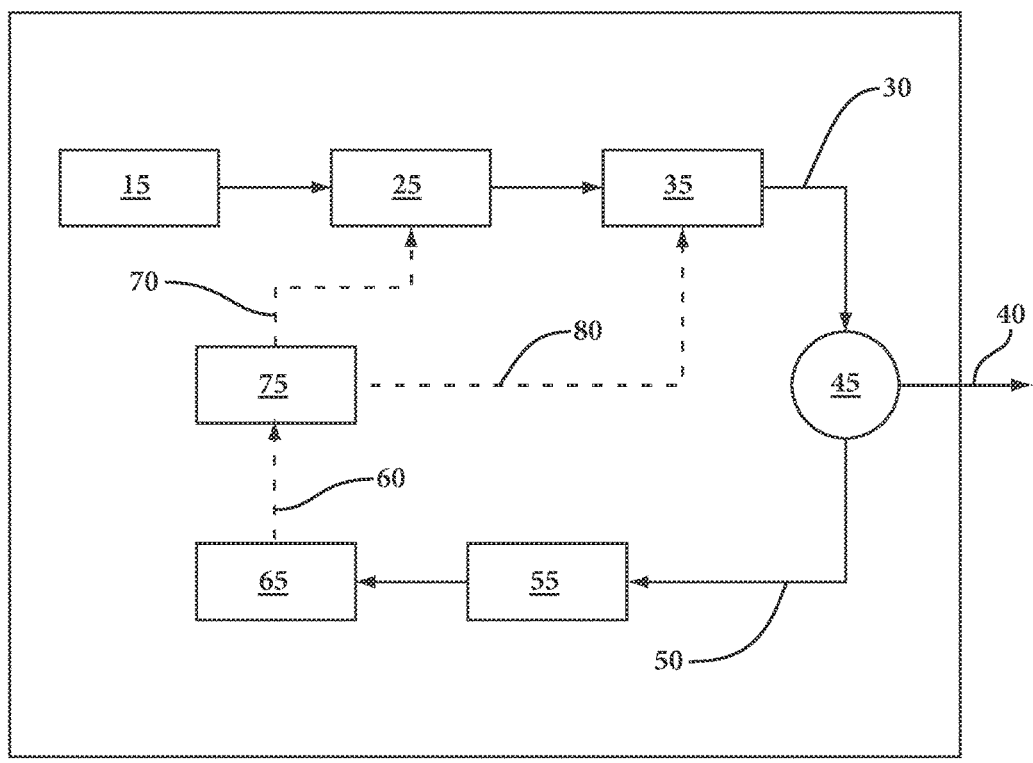
FIG. 1 illustrates a prior art high-level optical interrogator schematic.

We refer first to a high-level optical interrogator schematic provided in FIG. 1, labeled as prior art. The diagram provided in FIG. 1 is given as an example for discussion only and does not represent the properties or components of all possible fiber optic interrogator designs. The important principle to note is that such systems can be divided into a light-emitting path (upper path), and a light-receiving path (lower path). The light-emitting path performs the functions of sending the out-going or interrogating light signal into a region of interest and the light-receiving path receives an incoming or returned signal for measurement and processing. The upper path usually begins with the light source 15, often a laser. In the case of pulsed laser systems an optical amplifier 25 and an optical pulse generator 35 may follow this. The resulting pulsed light source 30 then passes to a passive optical device 45 for separating the interrogating pulsed light source light from any returning light. The outgoing light pulse source 40 then travels out into the region of interest for sensing. The returned light source, representing backscattered light signals from the region of interest also enters passive optical device 45 and is redirected 50 into the light-receiving path (lower path). Passive optical device 45 may be a coupler, a splitter, or a non-reciprocal optical device like a circulator or wavelength division multiplexer (WDM). It will be referred to in this disclosure as a circulator/coupler. It should be noted that optical amplifier 25, pulse generator 35, and laser 15 may be separate components, or combined into a single component with the amplifier and pulser being optional. Additional optical amplifiers, switches, filters, etc., may also be present in the light emitting path and may require control signals in order to operate properly.

Turning now to the light-receiving path (lower path) the returned back-scattered signals 50 from the region of interest are fed to an optical receiver/detector 55 that may contain photo-detectors as well as hardware and/or software needed to detect and analyze the returned signals. The analog signals from receiver/detector 55 may then pass to an analog-to-digital (ADC) converter 65 that feeds back 60 into an electronic controller 75.

The electronic controller 75 may act to control the operating parameters of the optical components. The electronic controller can be one or more of a microprocessor, field programmable gate array (FPGA), application specific integrated circuit (ASIC), operational amplifiers, comparators, or any other electrical components capable of providing control signals. One control signal 70 from electronic controller 75 may consist of parameters like the gain of an amplifier, which may be given as a voltage level or digitally encoded as a command sent to the amplifier module to control optical power emitted by the amplifier, for example, an erbium-doped fiber amplifier (EDFA). Another control signal 80 may be a timing signal in the form of a rising or falling edge of an electrical pulse sent to the optical pulse generator to control the timing and length of any optical pulses emitted by the pulse generator that may, for example, be in the form of a semiconductor optical amplifier (SOA).

Figure 2:
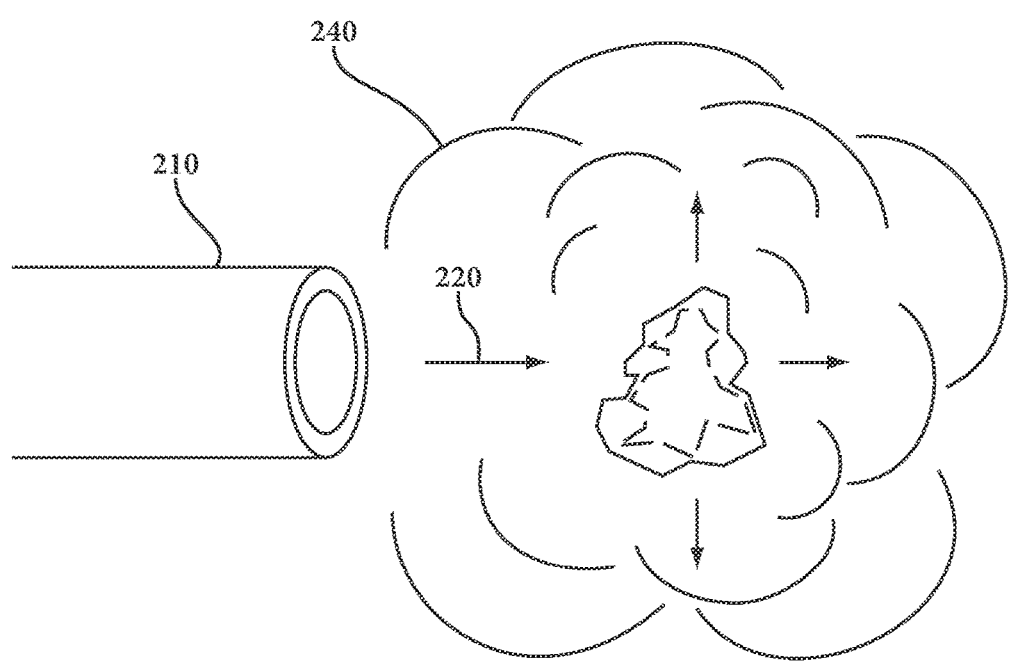
FIG. 2 illustrates the hazardous potential of an intense light signal striking a dust particle in an explosive gas mixture.

As mentioned previously, an earlier unrecognized danger in some fiber sensor interrogator systems is the ignition possibilities if the light energy exits the fiber and strikes a dust particle in an explosive atmosphere. FIG. 2 illustrates that potential in which light 220 exiting an optical fiber 210 could quickly be absorbed by a dust particle 230 in an explosive atmosphere 240 and due to the low surface area of the particle heat could accumulate in the particle rapidly until it reaches a high enough temperature to cause ignition.

Figure 3:
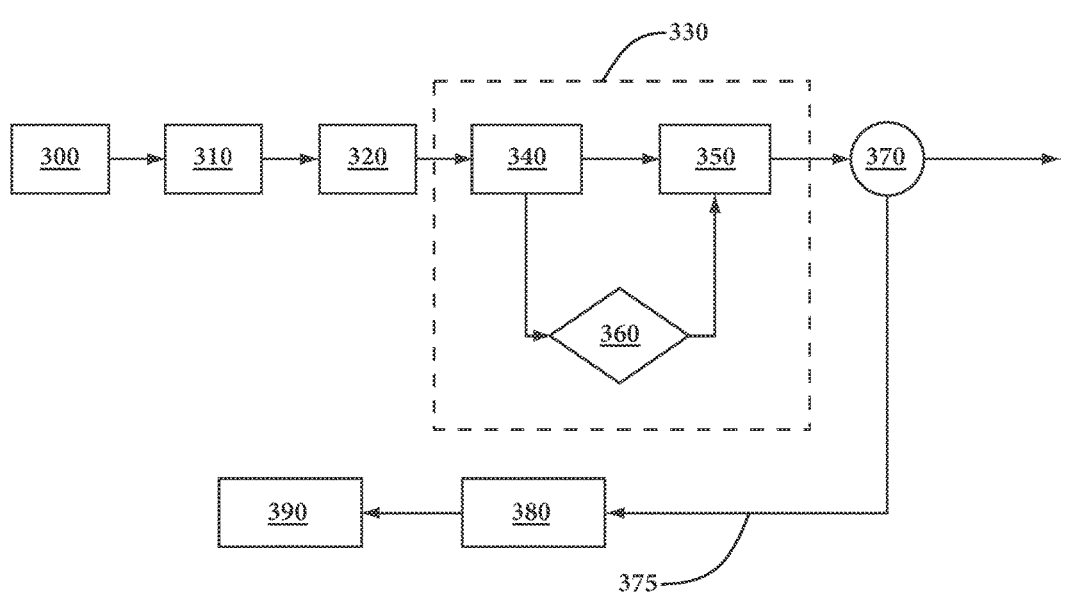
FIG. 3 illustrates a prior art optical electronic safety circuit.

The diagram of FIG. 3 provides an example of a prior art safety method used in fiber optic telecom systems. In this particular telecom system is shown a laser 300 feeding through a semiconductor optical amplifier (SOA) 310 and an erbium-doped fiber amplifier (EDFA) 320. In this approach an optical safety circuit 330 is inserted in the scheme before a circulator 370. Safety Circuit 330 uses a power meter 340 to monitor the energy level and via a control circuit 360 an optical switch or variable optical attenuator (VOA) 350 adjusts the power of the outgoing light. In this type of telecom system returned light 375 enters a receiver EDFA 380 and on to detector 390. As mentioned previously a disadvantage of such prior art optical safety circuit methods is that each component of the optical safety circuit is an active device with a possible failure mode. If any one of these three components were to fail to operate properly, the safety mechanism may fail to operate. The use of such systems requires testing and approval from a certification body, which can be a costly exercise.

Figure 4:
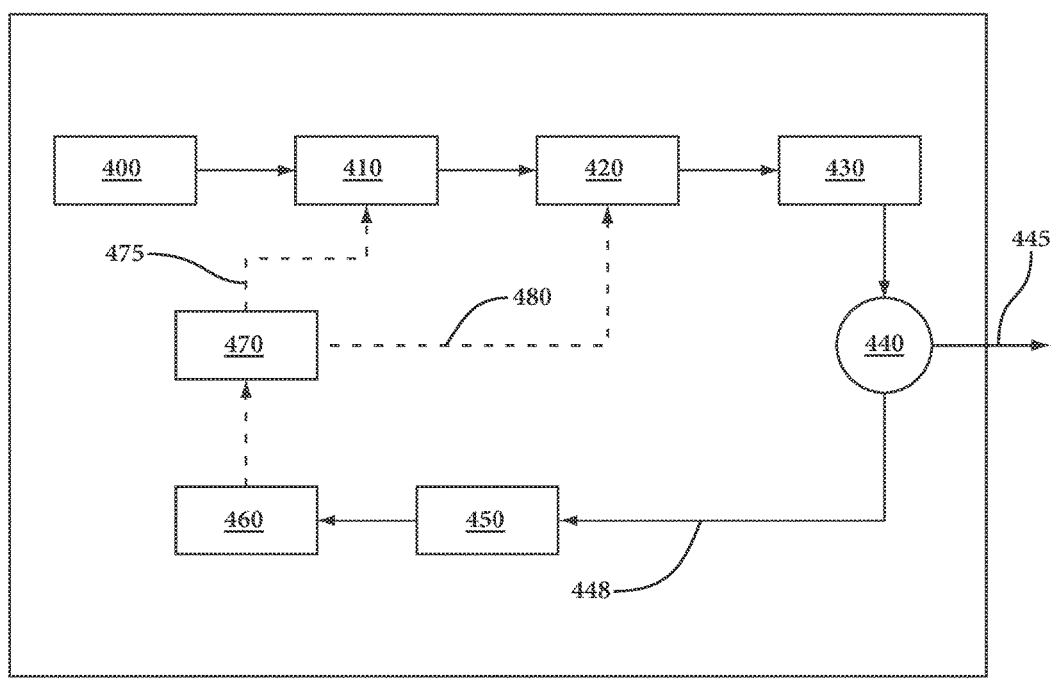
FIG. 4 illustrates the use of a passive optical power limiter employed in a fiber optic sensor interrogator system to provide enhanced safety.

The proposal of this disclosure is to provide a method of designing a much safer fiber sensor interrogator than the prior art method. The safety method of this proposal can be shown in FIG. 4. FIG. 4 exhibits an upper light emitting path and involves placing an intrinsic and passive optical power limiter 430 in the light-emitting upper path of the interrogator system such that the power limiter has a power threshold above which optical power is absorbed, scattered, or reflected by the device. As described previously the light emitting path may consist of a laser 400, an optical amplifier 410, and an optical pulse generator 420, all located before passive optical power limiter 430. As mentioned previously, the light emitting path may also be a laser only in the case of continuous wave (CW) systems or naturally pulsed laser systems. Device 430 is a fully passive optical device that may consist of a range of materials that act in a way to absorb, refract, or reflect light power when the power exceeds certain threshold values. The device may have a fixed attenuation to the optical energy passing through it when the optical power level is below a threshold and have a larger attenuation when the optical energy passing through it is above a threshold. As the input power into the device increases beyond the threshold level, the power that is transmitted through the device will remain at or near the threshold level or fall off depending on the type of device used. The device attenuation may be fully reversible when power levels return to below the threshold level or may be in a permanently high attenuation state after the high power event, thus acting as an optical fuse. Additionally, and importantly, device 430 will be located in the interrogator system such that it only affects the light emitted by the interrogator light from the light-emitting path, but has no effect on the sensor light that is returning to the interrogator and is directed to the light-receiving path. This is important because the sensing light returning to the interrogator is typically weaker than the transmitted light and may even be many orders of magnitude weaker than the transmitted light, and thus any additional attenuation will degrade the sensing signal. Additionally, any disturbance to the returned light through mechanisms like wavelength selective attenuation or other non-linear effects may negatively affect sensing parameters like accuracy, resolution, and repeatability. FIG. 4 provides an example optical schematic of the intrinsically safe fiber optic sensor interrogator.

Turning now to the light-receiving path (lower path) the returned back-scattered signals 448 from the region of interest 445 are fed to an optical receiver/detector 450 that may contain photo-detectors as well as hardware and/or software needed to detect and analyze the returned signals. The analog signals from receiver/detector 450 may then pass to an analog-to-digital (ADC) converter 460 that feeds back 465 into an electronic controller 470.

The electronic controller 470 may act to control the operating parameters of the optical components. The electronic controller can be one or more of a microprocessor, field programmable gate array (FPGA), application specific integrated circuit (ASIC), operational amplifiers, comparators, or any other electrical components capable of providing control signals. One control signal 475 from electronic controller 470 may consist of parameters like the gain of an amplifier, which may be given as a voltage level or digitally encoded as a command sent to the amplifier module to control optical power emitted by the amplifier, for example, an erbium-doped fiber amplifier (EDFA). Another control signal 480 may be a timing signal in the form of a rising or falling edge of an electrical pulse sent to the optical pulse generator to control the timing and length of any optical pulses emitted by the pulse generator that may, for example, be in the form of a silicon-optical amplifier (SOA).

The key element is the placement of optical power limiter 430 in the light-emitting path only and located before a passive optical device 440 for separating the outgoing light interrogating light from the incoming returned light. Device 440 again may be a coupler, a splitter, or a non-reciprocal optical device like a circulator or wavelength division multiplexer (WDM). It will be referred to in this disclosure as a circulator/coupler. Another important aspect of the design is that the optical power limiter is subsequent in the optical path to any optical elements that may increase the optical power emitted by the system. For example, optical amplifiers, pulse generators, switches, variable attenuators. The system may also contain more than one optical power limiter to guard against different types of faults. For example, one type of optical power limiter may be advantageous for limiting the power of continuous wave (CW) emitted light, but have a slow response time, whereas another kind of power limiter may be advantageous for use with high power pulses, but provide less protection for lower instantaneous power from continuous wave emission. By combining the fast responding power limiter to protect against high energy pulses, and a slower responsive power limited designed for lower power continuous wave emission, a superior solution may be provided.

Optical Power Limiters

Several possible different approaches for creation of an effective passive optical power limiter or optical fuse in a fiber interrogator system are anticipated in this disclosure. A passive optical power limiter or optical fuse can use reversible absorption materials. A known example of this is shown in WO 2012/077075, published Jun. 14, 2012, which describes an optical power-limiting device using the principle of absorption changes in a fast response photochromic material. A passive optical power limiter or optical fuse can also make use of materials that provide changes in refraction when threshold limits are exceeded. An optical limiter of this type has been described in US Patent application publication 2010/0166368, published Jul. 1, 2010. This particular approach used an optical grating comprising alternating layers of transparent dielectric materials and intervening layers in which light absorbing nano-particles are suspended in the dielectric matrix. If the interrogating light power passing through these layers goes above a threshold level the particles will absorb enough heat to conduct heat to the surrounding matrix and create alternating layers having different indices of refraction and thus create both backscattered and forward light components, reducing the forward light flux.

A passive optical power limiter or optical fuse can also make use of materials that impact transparency or reflectivity when threshold limits of power are exceeded. U.S. Pat. No. 6,218,658, issued Apr. 17, 2001 for example describes several embodiments of optical fuses employing thermally degradable portions with transparency and reflectivity positioned in contact with a light heatable portion that generates heat when light power striking it exceeds a threshold value. The resultant heat then degrades the thermally degradable portion, causing it to lose it transparency and reflectivity.

Any of these approaches making use of changes in absorption, refraction, or reflection based on physical properties of selected materials are anticipated for use in the passive optical power limiter or fuse described in this disclosure as being located after the light emitting path and before the circulator/coupler as shown in FIG. 4. Because all of these passive approaches are based on physical property behavior of known materials they react in a predictable manner and there is no "electronic failure mode" for the Optical Power Limiter.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

The invention claimed is:

1. In a fiber optic sensor interrogation system that includes at least a light emitting path for sending interrogation light signals and a light receiving path for receiving returned light signals, a method for enhancing safety by:
   a. sending the interrogation light signals from the light emitting path through a circulator/coupler device out into a region of interest to be measured;
   b. returning backscattered light from the region of interest through the circulator/coupler device into the light receiving path; and
   c. locating a passive power limiting device in the light emitting path and before the circulator/coupler device, wherein the passive power limiting device limits power of the light signals to below an ignition level in the region of interest.

2. The method for enhancing safety of claim 1 wherein the returning of backscattered light from the region of interest through the circulator/coupler into the light receiving path further includes at least;
  a. feeding the backscattered light into an optical receiver/detector to detect and analyze the returned signals.

3. The method for enhancing safety of claim 1 wherein the method of the passive power limiting device limits the power by absorption of the light signal when the light signal exceeds a threshold power value indicative of the ignition level.

4. The method for enhancing safety of claim 1 wherein the method of the passive power limiting device limits the power by refraction of the light signal when the light signal exceeds a threshold power value indicative of the ignition level.

5. The method for enhancing safety of claim 1 wherein the method of the passive power limiting device limits the power by reflection of the light signal when the light signal exceeds a threshold power value indicative of the ignition level.

6. The method for enhancing safety of claim 1 wherein the sending of the interrogation light signals includes at least;
  a. providing a light signal;
  b. providing optical amplification to that light signal.

7. The method for enhancing safety of claim 6 wherein the sending of the interrogation light signals further comprises;
  a. providing pulse generation to that light signal.

8. The method for enhancing safety of claim 7 wherein the returning of backscattered light from the region of interest through the circulator/coupler into the light receiving path further includes at least;
  a. feeding the backscattered light into an optical receiver/detector to detect and analyze the returned signals.

9. The method for enhancing safety of claim 7 wherein the method of the passive power limiting device limits the power by absorption of the light signal when the light signal exceeds a threshold power value indicative of the ignition level.

10. The method for enhancing safety of claim 7 wherein the method of the passive power limiting device limits the power by refraction of the light signal when the light signal exceeds a threshold power value indicative of the ignition level.

11. The method for enhancing safety of claim 7 wherein the method of the passive power limiting device limits the power by reflection of the light signal when the light signal exceeds a threshold power value indicative of the ignition level.

12. A fiber optic sensor interrogation system with inbuilt passive power limiting capability comprising:
  a. a light source;
  b. optical amplification circuitry acting on that light source;
  c. pulse generation circuitry acting on that amplified light source;
  d. wherein the light source, optical amplification circuitry and pulse generation circuitry represent a light emitting path for the fiber optic interrogation system;
  e. a circulator/coupler that directs light from the light emitting path for the fiber optic interrogation system into a region of interest for sensing, and receives and redirects backscattered light from the region of interest to a light receiving path;
  f. a passive power limiting device located in the light emitting path and before the circulator/coupler, wherein the passive power limiting device limits power of the light signals to below an ignition level in the region of interest.

13. The fiber optic sensor interrogation system with inbuilt passive power limiting capability of claim 12 further comprising:
  a. an optical receiver/detector that receives the redirected backscattered light from the region of interest.

14. The fiber optic sensor interrogation system with inbuilt passive power limiting capability of claim 13 further comprising:
  a. an electronic control system for providing control parameters to the optical amplification circuitry acting on the light source and the pulse generation circuitry acting on the light source.

15. The fiber optic sensor interrogation system with inbuilt passive power limiting capability of claim 12 wherein the passive power limiting device limits the power by absorption of the light signal when the light signal exceeds a threshold power value indicative of the ignition level.

16. The fiber optic sensor interrogation system with inbuilt passive power limiting capability of claim 12 wherein the passive power limiting device limits the power by refraction of the light signal when the light signal exceeds a threshold power value indicative of the ignition level.

17. The fiber optic sensor interrogation system with inbuilt passive power limiting capability of claim 12 wherein the passive power limiting device limits the power by reflection of the light signal when the light signal exceeds a threshold power value indicative of the ignition level.

18. The fiber optic sensor interrogation system with inbuilt passive power limiting capability of claim 12 wherein the laser, optical amplification circuitry and pulse generation circuitry are combined into a single component.

19. The fiber optic sensor interrogation system with inbuilt passive power limiting capability of claim 18 further comprising:
  a. an optical receiver/detector that receives the redirected backscattered light from the region of interest.

20. The fiber optic sensor interrogation system with inbuilt passive power limiting capability of claim 18 wherein the passive power limiting device limits the power by absorption of the light signal when the light signal exceeds a threshold power value indicative of the ignition level.

21. The fiber optic sensor interrogation system with inbuilt passive power limiting capability of claim 18 wherein the passive power limiting device limits the power by refraction of the light signal when the light signal exceeds a threshold power value indicative of the ignition level.

22. The fiber optic sensor interrogation system with inbuilt passive power limiting capability of claim 18 wherein the passive power limiting device limits the power by reflection of the light signal when the light signal exceeds a threshold power value indicative of the ignition level.

23. A fiber optic sensor interrogation system with inbuilt passive power limiting capability comprising:
  a. a light source;
  b. a circulator/coupler that directs light from a light emitting path for the fiber optic interrogation system into a region of interest for sensing, and receives and redirects backscattered light from the region of interest to a light receiving path;
  c. a passive power limiting device in the light emitting path located after the light source and before the circulator/coupler, wherein the passive power limiting device limits power of the light signals to below an ignition level in the region of interest.

24. The fiber optic sensor interrogation system with inbuilt passive power limiting capability of claim 23 further comprising:
   a. an optical receiver/detector that receives the redirected backscattered light from the region of interest.

25. The fiber optic sensor interrogation system with inbuilt passive power limiting capability of claim 23 wherein the passive power limiting device limits the power by absorption of the light signal when the light signal exceeds a threshold power value indicative of the ignition level.

26. The fiber optic sensor interrogation system with inbuilt passive power limiting capability of claim 23 wherein the passive power limiting device limits the power by refraction of the light signal when the light signal exceeds a threshold power value indicative of the ignition level.

27. The fiber optic sensor interrogation system with inbuilt passive power limiting capability of claim 23 wherein the passive power limiting device limits the power by reflection of the light signal when the light signal exceeds a threshold power value indicative of the ignition level.

* * * * *